United States Patent [19]
Yufa

[11] Patent Number: 5,767,967
[45] Date of Patent: Jun. 16, 1998

[54] METHOD AND DEVICE FOR PRECISE COUNTING AND MEASURING THE PARTICULATES AND SMALL BODIES

[76] Inventor: Aleksandr L. Yufa, P.O. Box 1677, Colton, Calif. 92324

[21] Appl. No.: 778,036

[22] Filed: Jan. 2, 1997

[51] Int. Cl.[6] .................................................. G01N 15/02
[52] U.S. Cl. ........................... 356/336; 356/339; 356/343; 250/574; 250/458.1
[58] Field of Search .................................. 356/335–343, 356/236, 73, 317, 301, 39; 250/574, 575, 573, 458.1, 461.2

[56] References Cited

U.S. PATENT DOCUMENTS

| | | | |
|---|---|---|---|
| 4,188,543 | 2/1980 | Brunsting et al. | 356/339 |
| 4,189,236 | 2/1980 | Hogg et al. | 356/336 |
| 4,422,761 | 12/1983 | Frommer | 356/338 |
| 4,523,841 | 6/1985 | Brunsting et al. | 356/73 |
| 5,043,591 | 8/1991 | Ludlow et al. | 356/343 |
| 5,089,714 | 2/1992 | Ludlow et al. | 356/343 |
| 5,127,729 | 7/1992 | Oetliker et al. | 356/338 |
| 5,467,189 | 11/1995 | Kreikebaum et al. | 356/336 |
| 5,471,299 | 11/1995 | Kaye et al. | 356/336 |

*Primary Examiner*—Hoa Q. Pham

[57] ABSTRACT

A device for counting and measuring the particles provides a precise analysis of the particle characteristics and includes an ellipsoidal mirror system, having two different sizes ellipsoidal concentric mirrors (4) and (5) connected towards to each other by their cross-section lateral areas, and a first ellipsoidal mirror (4) is smaller than a second ellipsoidal mirror (5), includes also a light beam and a particulates flow passing inside the first ellipsoidal mirror (4) through a first focus of the first ellipsoidal mirror (4), concurred with a second focus of the second ellipsoidal mirror (5), also includes a light detector (20), which is placed inside the second ellipsoidal mirror (5) at a first focus of the second ellipsoidal mirror (5), concurred with a second focus of the first ellipsoidal mirror (4). An improved device comprises also an electronic control system, including an analog-digital subsystem (45) and a microprocessor subsystem (32), which provide the signal processing and control functions.

16 Claims, 14 Drawing Sheets

VIEW
61 - 61

VIEW
62 - 62

METHOD AND DEVICE FOR PRECISE COUNTING AND MEASURING THE PARTICULATES AND SMALL BODIES

FIELD OF THE INVENTION

This invention relates to the air quality and, more particularly, to devices and instruments for particle quantity counting and particle size measuring by light scattering.

BACKGROUND OF THE INVENTION

The methods and devices for determining quantity and size of the particles and small bodies now well known, and it is also well known that powerful light or laser and optical system or mirror can be, and have been, heretofore used to achieve particle size and particle quantity measurements. Such devices using light scattering are well known and described in the articles: R. G. Knollenberg, B. Schuster—"Detection and Sizing of Small Particles in Open Cavity Gas Laser," Applied Optics, Vo. 11, No. 7, November 1972, pp. 1515–1520; R. G. Knollenberg—"An Active Scattering Aerosol Spectrometer," Atmospheric Technology, No. 2, June 1973, pp. 80–81; R. G. Knollenberg—"Active Scattering Aerosol Spectrometry," National Bureau of Standards Special Publication, No. 412, October 1974, pp. 57–64; R. G. Knollenberg, R. E. Luehr—"Open Cavity Laser 'Active' Scattering Particle Spectrometry from 0.05 to 5.0 Microns," Fine Particles, Aerosol Generation Measurement, Sampling and Analysis, Academic Press, May 1975, pp. 669–696; R. G. Knollenberg—"Three New Instruments for Cloud Physics Measurements: The 2-D Spectrometer, the Forward Scattering Spectrometer Probe, and the Active Scattering Aerosol Spectrometer", American Meteorological Society, International Conference on Cloud Physics, July 1976, pp. 554–561; R. G. Knollenberg—"The Use of Low Power Laser in Particle Size Spectrometry", Proceeding of the Society of Photo-Optical Instrumentation Engineers, Practical Applications of Low Power Lasers, Vo. 92, August 1976, pp. 137–152; R. G. Knollenberg—"The Measurement of Particle Sizes Below 0.1 Micrometers", Journal of Environment Science, January-February, 1985, pp. 64–67.

The reference in these articles is made to the devices and methods of particulate measurement utilizing an open cavity laser. These methods and devices use the imaging systems which are based on lens use, the same as it mentioned, for example, in the U.S. Pat. No. 4,798,465 and in the U.S. Pat. No. 4,140,395 of the prior art. It is known, that the lens use in such devices is limited by quality of the lens material. A lens material should have high quality (like $SiO_2$), considering influence of high velocity of intensive particle flow inside measuring devices and the mass and size of particles. For instance, integrated circuits (chips) and semiconductors have been produced in known "clean rooms". The air in such "clean rooms" should be very well filtrated. The continuing tendencies of the improvement of circuit integration and degree of microminiaturization require corresponding improvements of the environment in "clean rooms" and efficiency of the measuring devices. As mentioned in prior art, most now known particle counting and measuring devices have at least one cubic foot per minute 1 (cfm) sample flow rates and a pressure up to 150 P.S.I. However, the development of semiconductors and integrate circuits (chips) industry leads to higher requirements for the particle measurement instruments and devices. And now, as known from prior art, to achieve reasonable statistics in Class 1 environment, it is necessary to assay many cubic feet per minute of air for the sensitivity related with 0.5 (μm) Microns particles. However, definitely, the airborne particles in "clean room" and inside measuring devices at the time of assaying will be presented by particles mixture with different particle sizes, but not 0.5 Microns only. If integrated circuit and semiconductor industries give more attention to small particles (from 0.1 Microns to 20–35 Microns), considering very well filtration of the air in "clean room", the some other industries (for example, chemical, pharmacological, etc.) still give some attention to medium and big sizes of particles and bodies (from 10–15 Microns to 70–100 Microns).

Thus, in the real practice the counting and measuring devices should be related to the particles and bodies with the following dimensions:

$$\left.\begin{array}{l}(0.1\ \mu m;\ 100\ \mu m)\\(M_{min};\ 0.1\ \mu m]\\\lbrack 100\ \mu m;\ M_{max})\end{array}\right\} \subseteq D, \qquad [1]$$

where D—the dimensions (the particle/body size);

$M_{min}$—minimal size of a particle (smaller than 0.1 μm) limited by sensitivity of the device;

$M_{max}$—maximal size of a particle (bigger than 100 μm) which can physically be measured by the means of the device.

It is known, that the lenses can be damaged (scratched, etc.) by 20–35 Microns and bigger particles. Additionally, the most common and important deficiency of the mentioned above methods and devices is they count the quantity of particles non-authentically (incorrectly). It is understood that maximum efficiency of such devices have not exceeded approximately 16.667%, because, these devices have not considered all scattered light, which is distributed around the scattering light source. The devices mentioned above count and measure the particles and small bodies in the one of six basics scattered light direction (in the direction to the location of the imaging system). It means that the devices have mentioned in the prior art, count and measure the particle quantity, which less than ⅙ (~16.667%) of total particle quantity, because only less than ~16.667% of the scattered light flows through the imaging system (lenses).

The other devices mentioned in prior art (for example, U.S. Pat. No. 4,606,636) have been used a non-divergent quadric reflector. These devices use a paraboloidal sphere as mirror and can have efficiency close to maximal value. However, all devices which use such method for counting and measuring of particles, need to use very big and an expensive detector. This is necessarily, because in practice the cross-diameter of the mirror achieves ~(1.5"–3.5"), considering at least 1(cfm) sample flow rates and the pressure up to 150 P.S.I. mentioned of the above. It is understood that in order for to achieve maximal efficiency, the dimensions and form of the detector in such devices should be adequate to the diameter of a non-divergent quadric reflector. To produce such detectors is very difficult and expensive.

Therefore, devices with the non-divergent quadric reflectors have not found the use in the particle measurement instruments and devices industry.

Yet in other prior art (for example, such as U.S. Pat. No. 4,523,841 and U.S. Pat. No. 5,467,189) we can find the devices (the sensors) with the elliptical mirrors instead the lens systems or the non-divergent mirrors. These devices use usually a half (or sometimes less) of the ellipse as the elliptical mirror and have not required a big, expensive detector as the devices with the non-divergent quadric mirrors. Such devices have much higher efficiency than devices with lens system, however, their efficiency is not satisfied too. Because, the existing known methods and devices with elliptical mirrors are unable to count and to measure all particles and small bodies of assaying air. Such devices have not considered the unreflected (by elliptical mirror) scattered light.

Some information about a prior art method and devices can be also obtained from: Peters—"20 Good Reasons to Use In Situ Particle Monitors", Semiconductor International, Nov. 1992, pp. 52–57; Busselman et al.—"In Situ Particle Monitoring in a Single Wafer Poly Silicon and Silicon Nitride Etch System", IEEE/SEMI Int'l Semiconductor Manufacturing Science Symposium, 1993, pp. 20–26 and U.S. Pat. No. 5,083,865 (02.28.92).

Thus, all methods and devices of a prior art have not considered the unreflected scattered light, which has never reached the detector. It means that not all particles and small bodies presented in the air composition of the "clean room" have been counted and measured by the existing devices of the prior art. Another and very important negative characteristic of the methods and devices of all prior art is the noises. The unconsidered (undetected) scattered light creates the light background (light noises) in the detector area (near a detector), creating incorrectness of resulting information about outside environment and additionally light noise limits the sensitivity of such devices.

OBJECT AND ADVANTAGES OF THE INVENTION

Accordingly, several objects and advantage of the present invention are to provide an improved method and device for counting and measuring the particulates and small bodies.

It is another object of the invention to provide an improved method and device for increasing the precision of particulates and small bodies counting and measuring.

It is still another object of the invention to provide an improved method and device for increasing the efficiency of the measuring and counting process result.

It is still further object of the invention to provide an improved method and device for increasing the authenticity of the information about air composition.

It is yet another object of the invention to provide an improved method and device to decrease light noises by eliminating undetected scattered light background inside an improved device.

It is yet further object of the invention to provide an improved method and device capable of providing high sensitivity.

It is another further object of the invention to provide an improved method and device that eliminates light noises (background noises) due to molecular scattering to a level that allows counting and measuring of particulate sizes at least as small as 0.1 Micron in high molecular scattering environments.

It is still another object of the invention to provide an improved method and device for self diagnostics and calibration.

Still, further objects and advantages will become apparent from a consideration of the ensuing description accompanying drawings.

Figure 1:
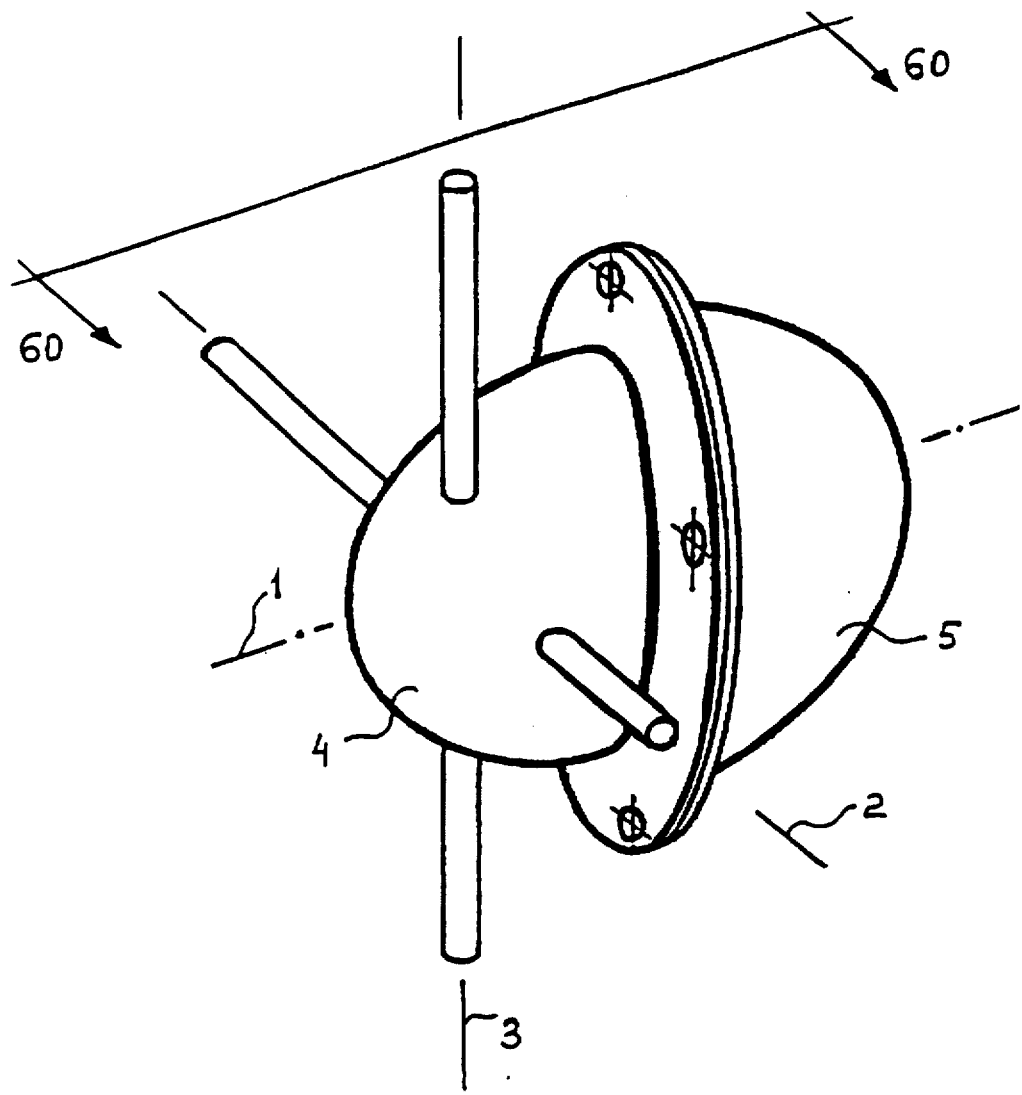
FIG. 1 is an isometric spatial representation of certain aspects of an improved method and device.

On FIG. 1 are shown: 1.—a device axis; 2.—a light beam axis; 3.—a particle flow axis; 4.—a first ellipsoidal mirror; 5.—a second ellipsoidal mirror.

Figure 2:
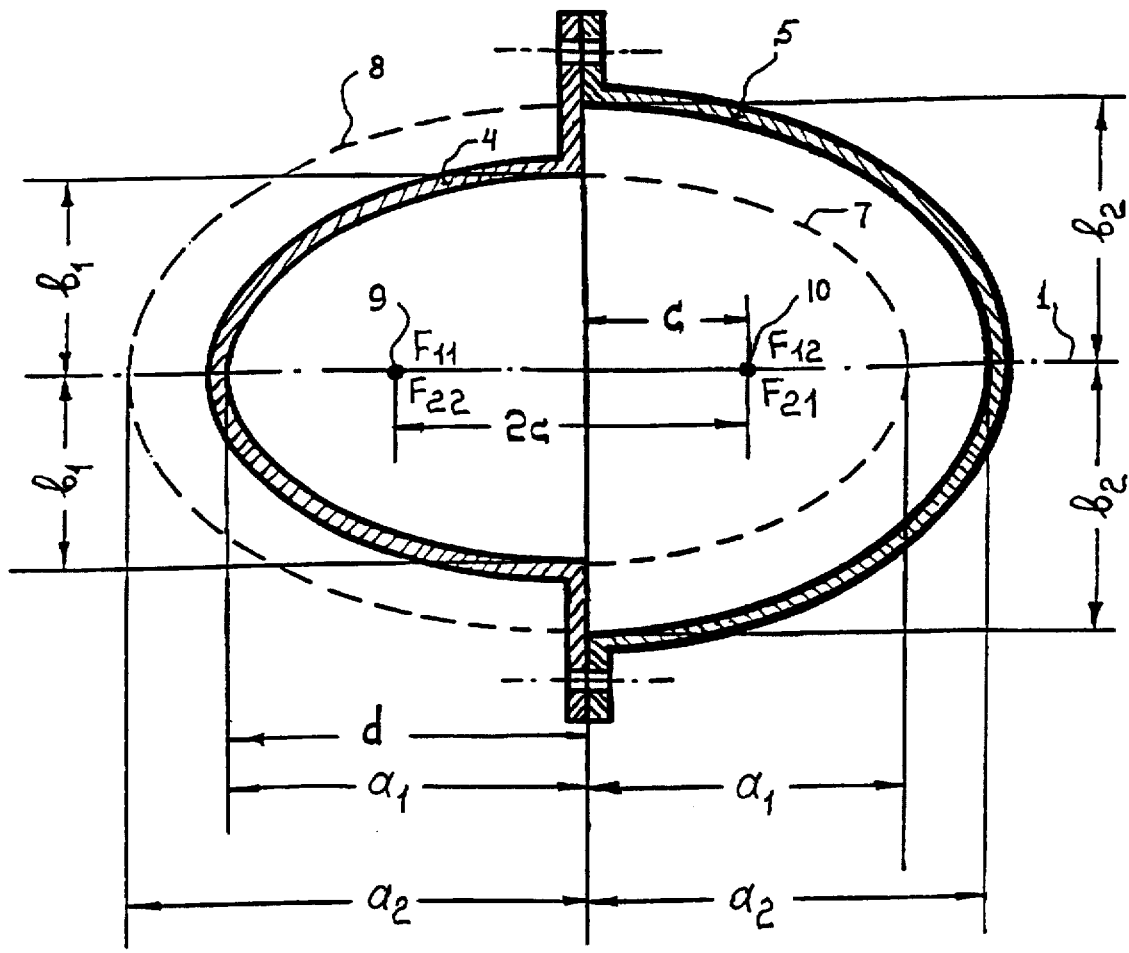
FIG. 2 illustrates the particularities of an ellipsoidal mirrors concentricity.

On FIG. 2 are shown: 1.—a device axis; 4.—a first ellipsoidal mirror; 5.—a second ellipsoidal mirror; 7.—a first ellipsoid; 8.—a second ellipsoid; 9.—a first focus ($F_{11}$) of the first ellipsoid 7 and a second focus ($F_{22}$) of the second ellipsoid 8; 10.—a second focus ($F_{12}$) of the first ellipsoid 7 and a first focus ($F_{21}$) of the second ellipsoid 8.

Figure 3:
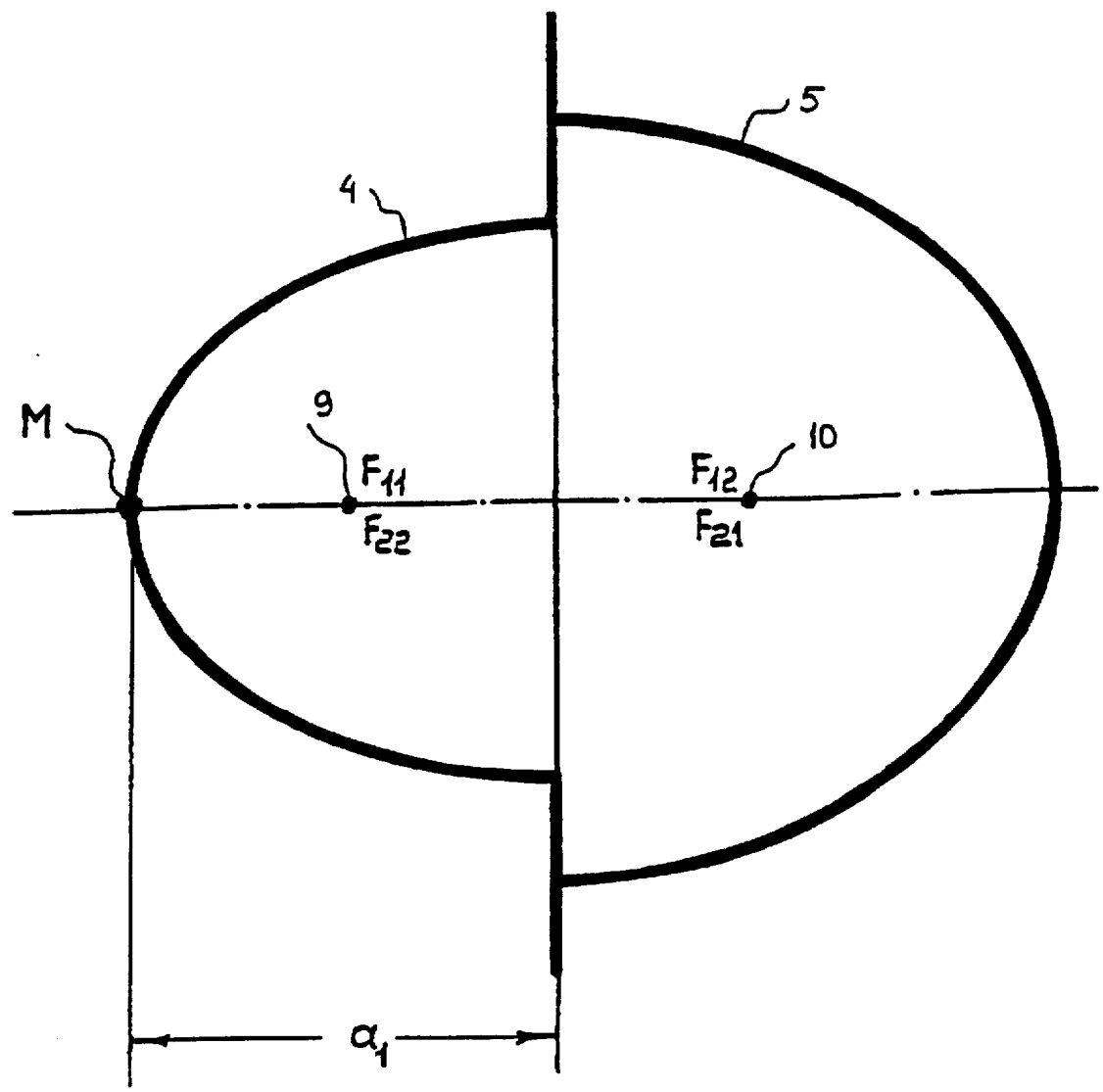
FIG. 3 is a simplified drawing of the first main variant of an improved device design.

On FIG. 3 are shown: 1.—a device axis; 4.—a first ellipsoidal mirror; 5.—a second ellipsoidal mirror; 9.—a first focus ($F_{11}$) of the first ellipsoidal mirror 4 and a second focus ($F_{22}$) of the second ellipsoidal mirror 5; 10.—a second focus ($F_{12}$) of the first ellipsoidal mirror 4 and a first focus ($F_{21}$) of the second ellipsoidal mirror 5.

Figure 4:
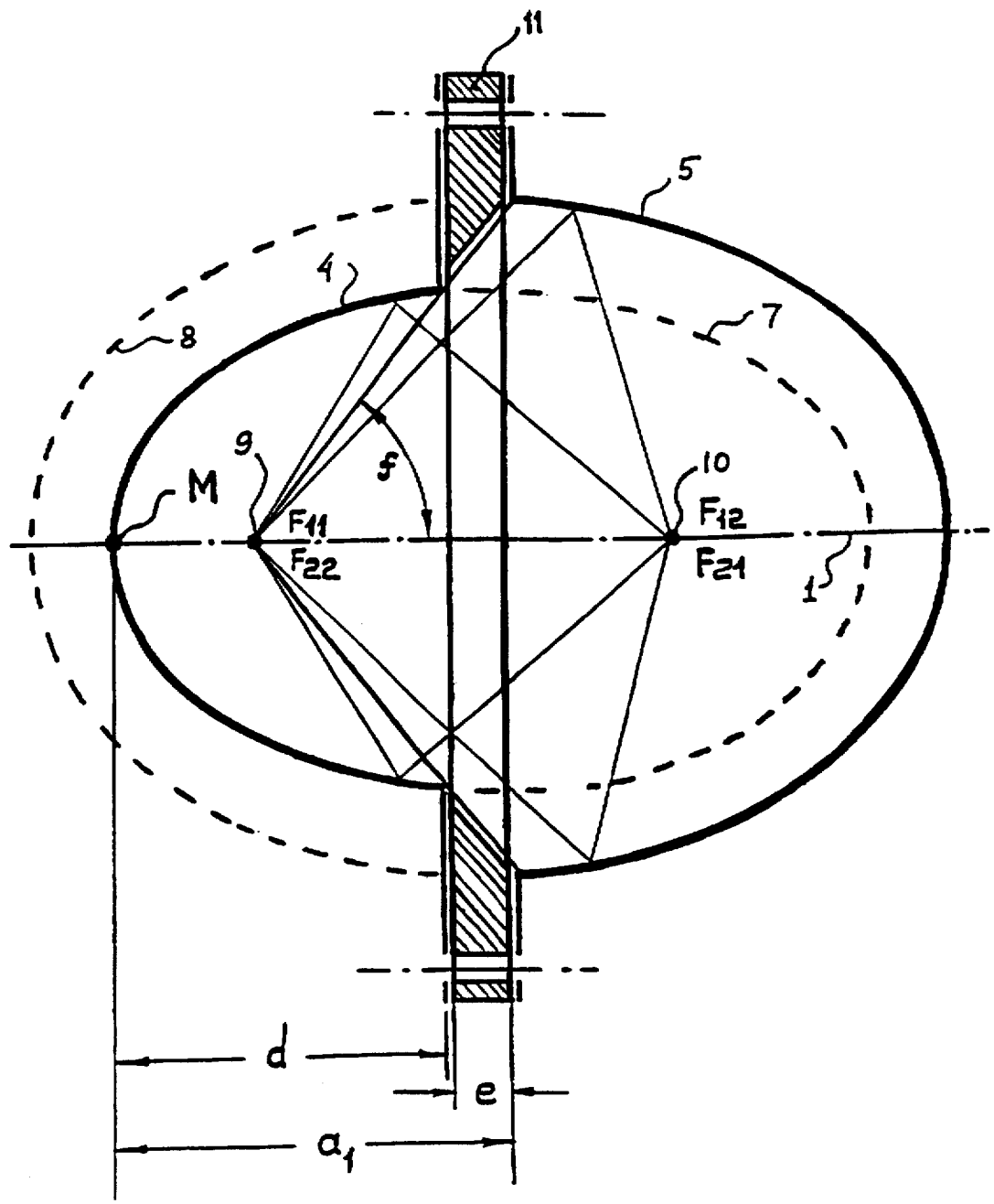
FIG. 4 is a simplified drawing of the second variant of an improved device design.

On FIG. 4 are shown: 1.—a device axis; 4.—a first ellipsoidal mirror, which is shorter than a half of the first ellipsoid; 5.—a second ellipsoidal mirror, 7.—a first ellipsoid; 8.—a second ellipsoid; 9.—a first focus ($F_{11}$) of the first ellipsoidal mirror 4 and a second focus ($F_{22}$) of the second ellipsoidal mirror 5, 10.—a second focus ($F_{12}$) of the first ellipsoidal mirror 4 and a first focus ($F_{21}$) of the second ellipsoidal mirror 5, 11.—an additional ring.

Figure 5:
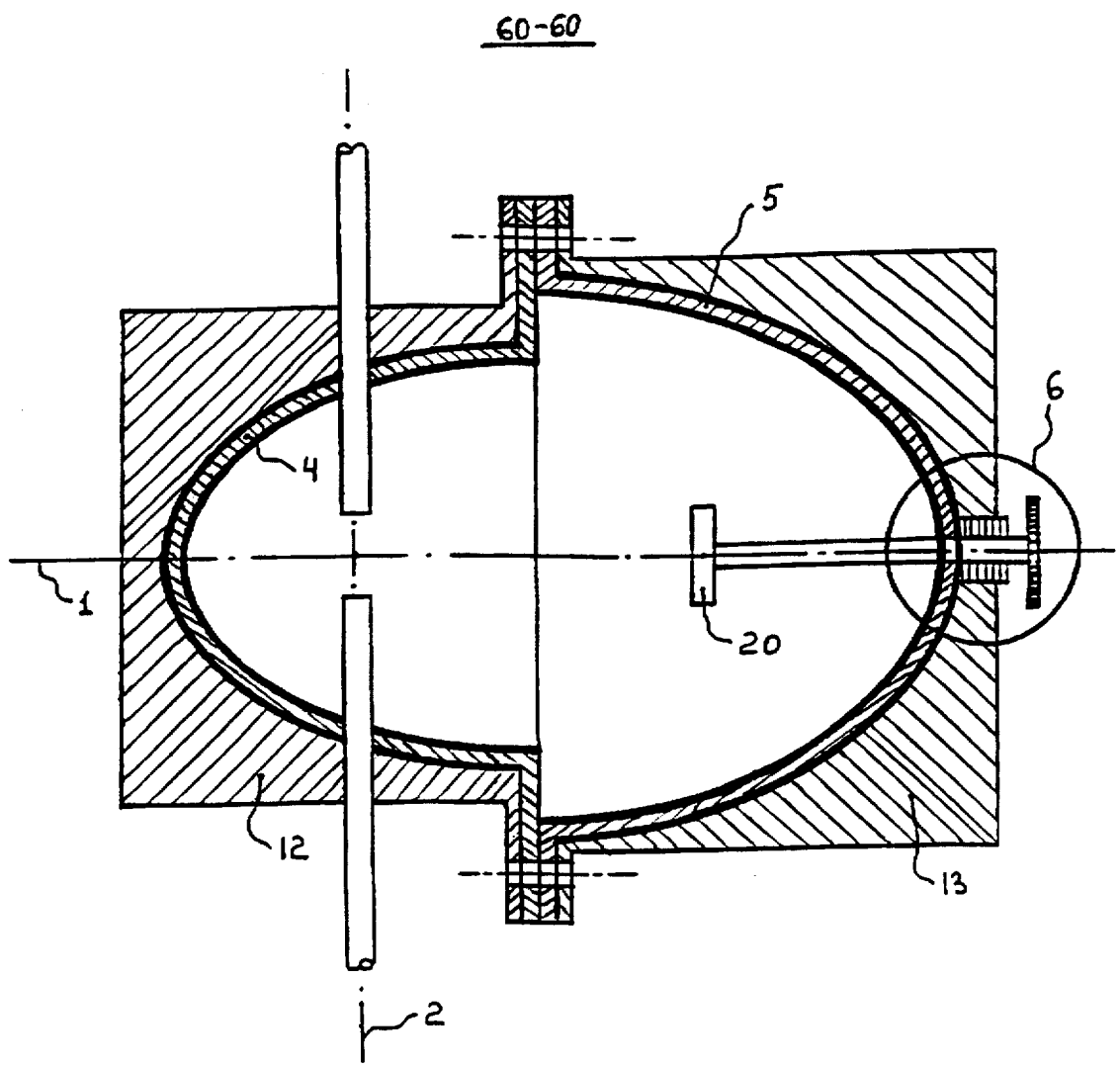
FIG. 5 is a cross-sectional simplified drawing of an improved method and device taken from the perspective of viewing axes 60—60 of FIG. 1 and including simplified housing of the components.

On FIG. 5 are shown: 1.—a device axis; 2.—a light beam axis; 4.—a first ellipsoidal mirror; 5.—a second ellipsoidal mirror; 6.—a detector affixture and adjustment means; 12.—a body of the first ellipsoidal mirror 4; 13.—a body of the second ellipsoidal mirror 5; 20.—a light detector.

Figure 6:
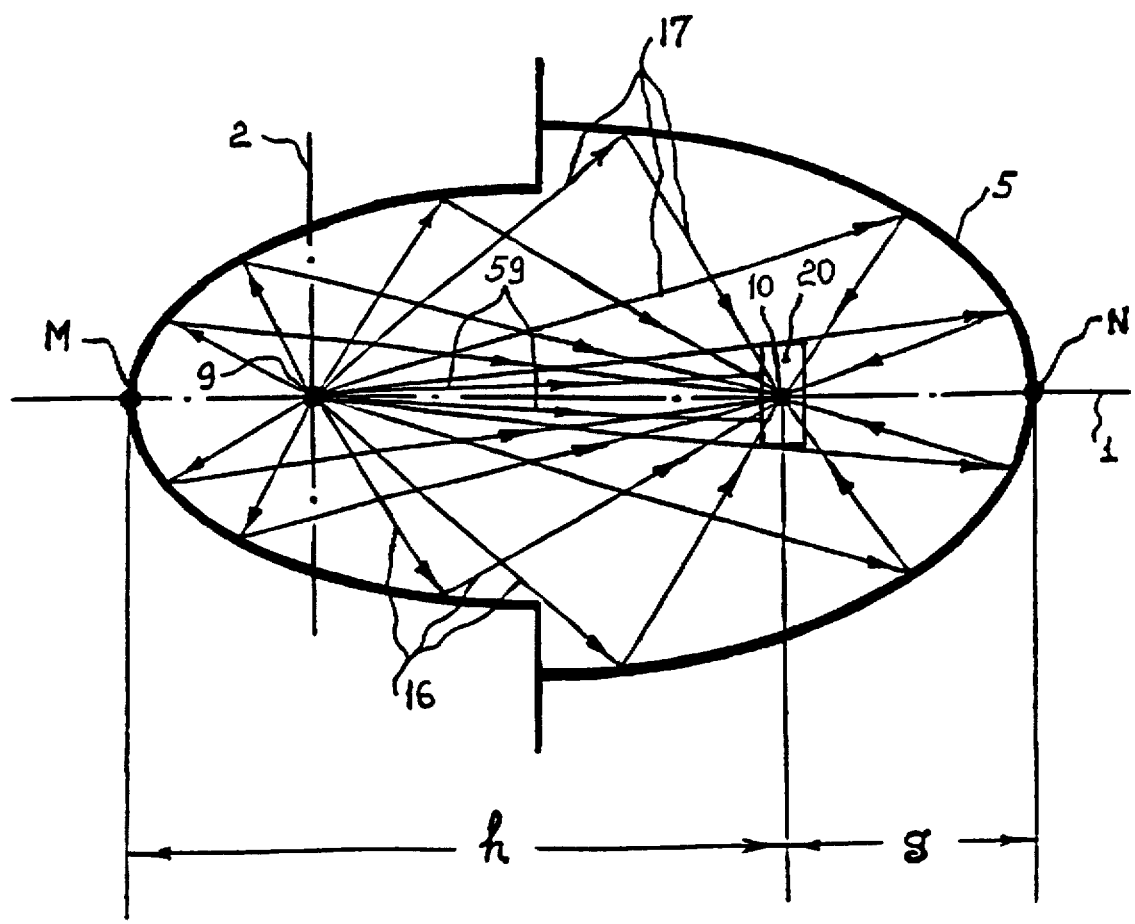
FIG. 6 is a simplified drawing (representation) of the scattered light distribution and detection by improved method in the improved device.

On FIG. 6 are shown: 1.—a device axis; 2.—a light beam axis; 4.—a first ellipsoidal mirror; 5.—a second ellipsoidal mirror; 9.—a first focus ($F_{11}$) of the first ellipsoidal mirror 4 and a first focus ($F_{22}$) of the second ellipsoidal mirror 5; 10.—a second focus ($F_{12}$) of the first ellipsoidal mirror 4 and a second focus ($F_{21}$) of the second ellipsoidal mirror 5, 16.—a scattered light reflected from the first ellipsoidal mirror 4; 17.—a scattered light reflected from the second ellipsoidal mirror 5; 20.—a light detector; 59.—an unreflected scattered light detected by the light detector 20 directly.

Figure 7:
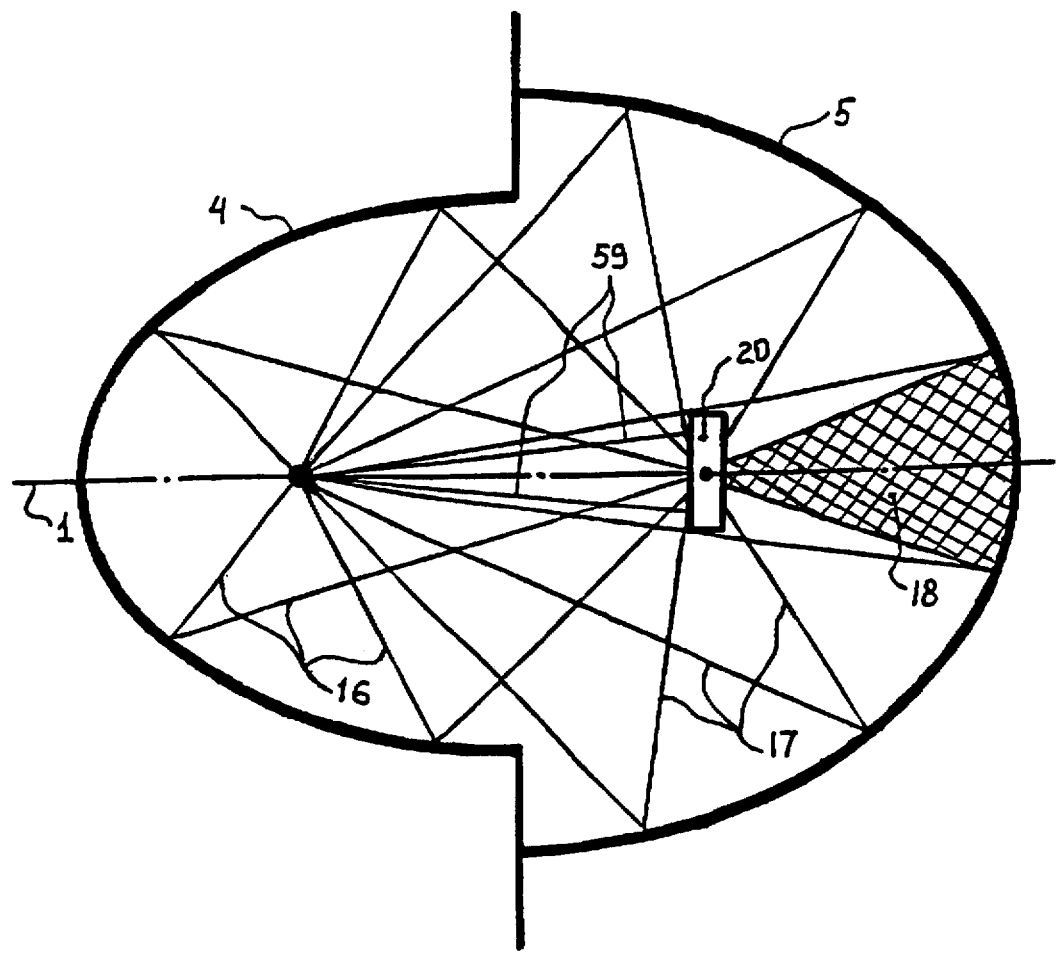
FIG. 7 illustrates an inactive zone of an ellipsoidal mirror system.

On FIG. 7 are shown: 1.—a device axis; 4.—a first ellipsoidal mirror; 5.—a second ellipsoidal mirror; 16.—a scattered light reflected from the first ellipsoidal mirror 4; 17.—a scattered light reflected from the second ellipsoidal mirror 5; 18.—a zone for affixing and adjusting of the light detector position; 20.—a light detector; 59.—an unreflected scattered light detected by the light detector 20 directly.

Figure 8:
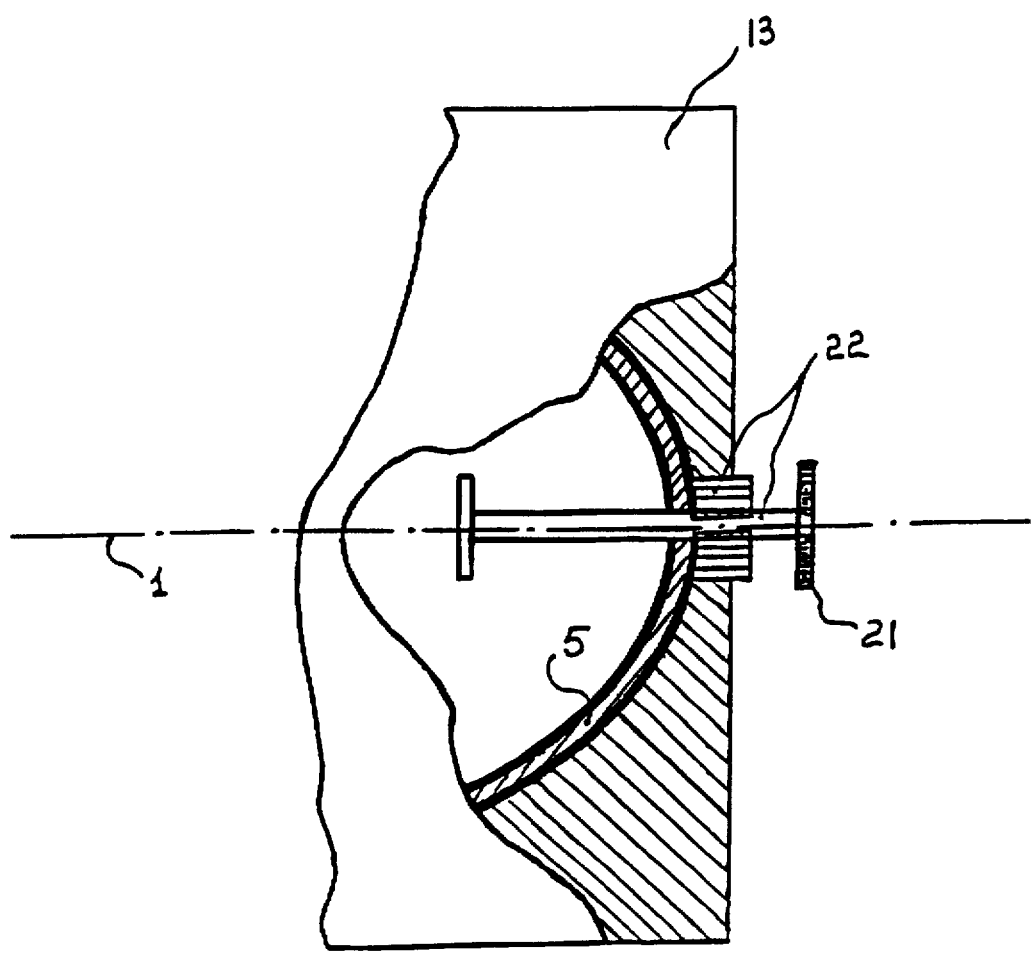
FIG. 8 is a simplified structural drawing of a detector affixture and adjustment means placing.

On FIG. 8 are shown: 1.—a device axis; 5.—a second ellipsoidal mirror; 6.—a detector affixture and adjustment means; 13.—a body of the second ellipsoidal mirror 5; 20.—a light detector; 21.—an organ of adjustment; 22.—a transmission means.

Figure 9:
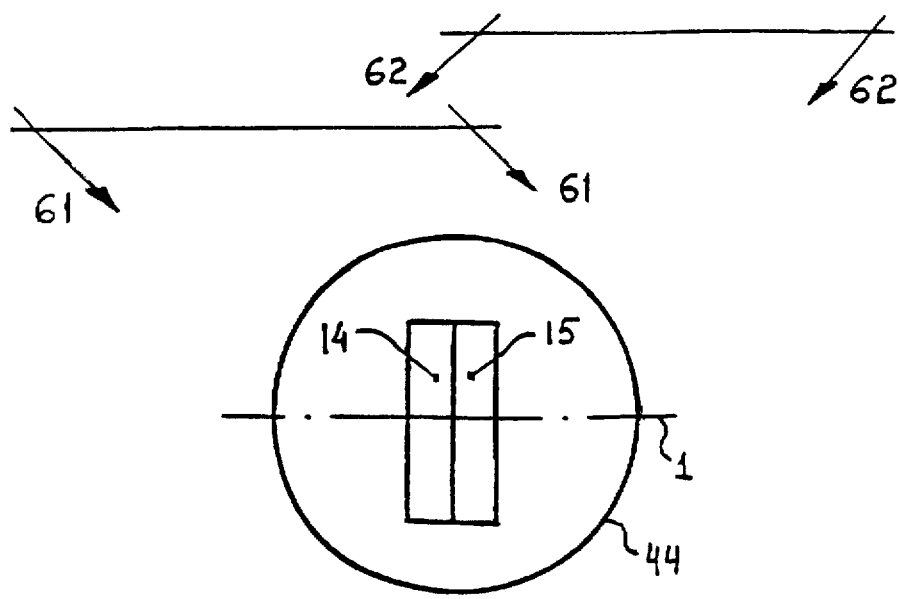
FIG. 9 illustrates a configuration of a detection means.
Figure 9:
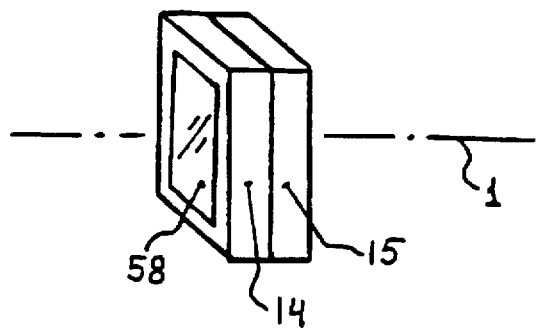
Figure 9:
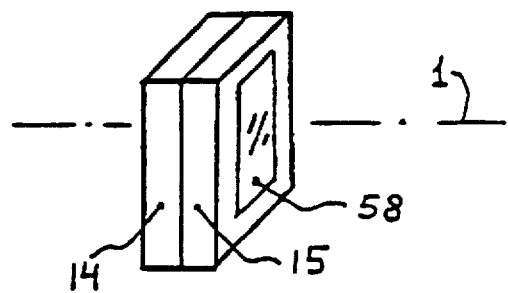

On FIG. 9 are shown: 1.—a device axis; 14.—a first light detector of the detection means 44;

15.—a second light detector of the detection means 44; 44.—a detection mean;. 58.—a photo element.

Figure 10:
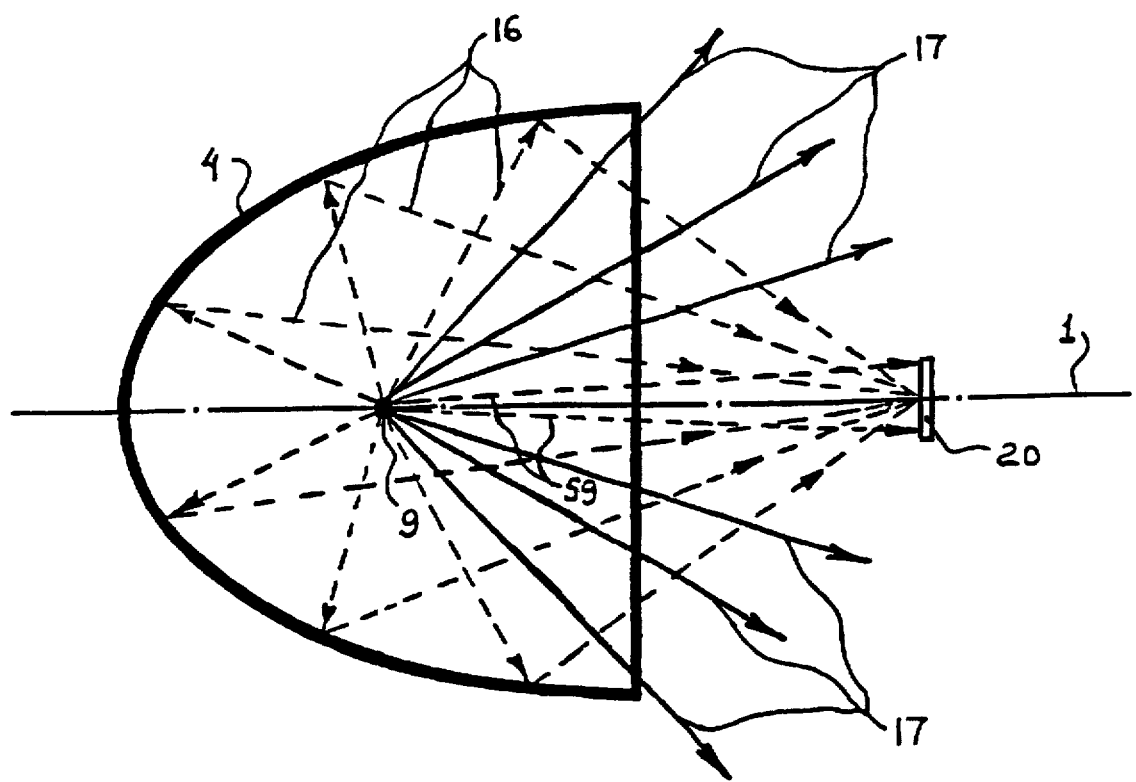
FIG. 10 illustrates a non-spatial directions of the scattered light distribution.

On FIG. 10 are shown: 1.—a device axis; 4.—a first ellipsoidal mirror; 9.—a first focus ($F_{11}$) of the first ellipsoidal mirror 4 and a second focus ($F_{22}$) of the second ellipsoidal mirror 5; 16.—a scattered light reflected from the first ellipsoidal mirror 4; 17.—a scattered light is reflected from the second ellipsoidal mirror 5; 20.—a light detector; 59.—an unreflected scattered light detected by the light detector 20 directly.

Figure 11:
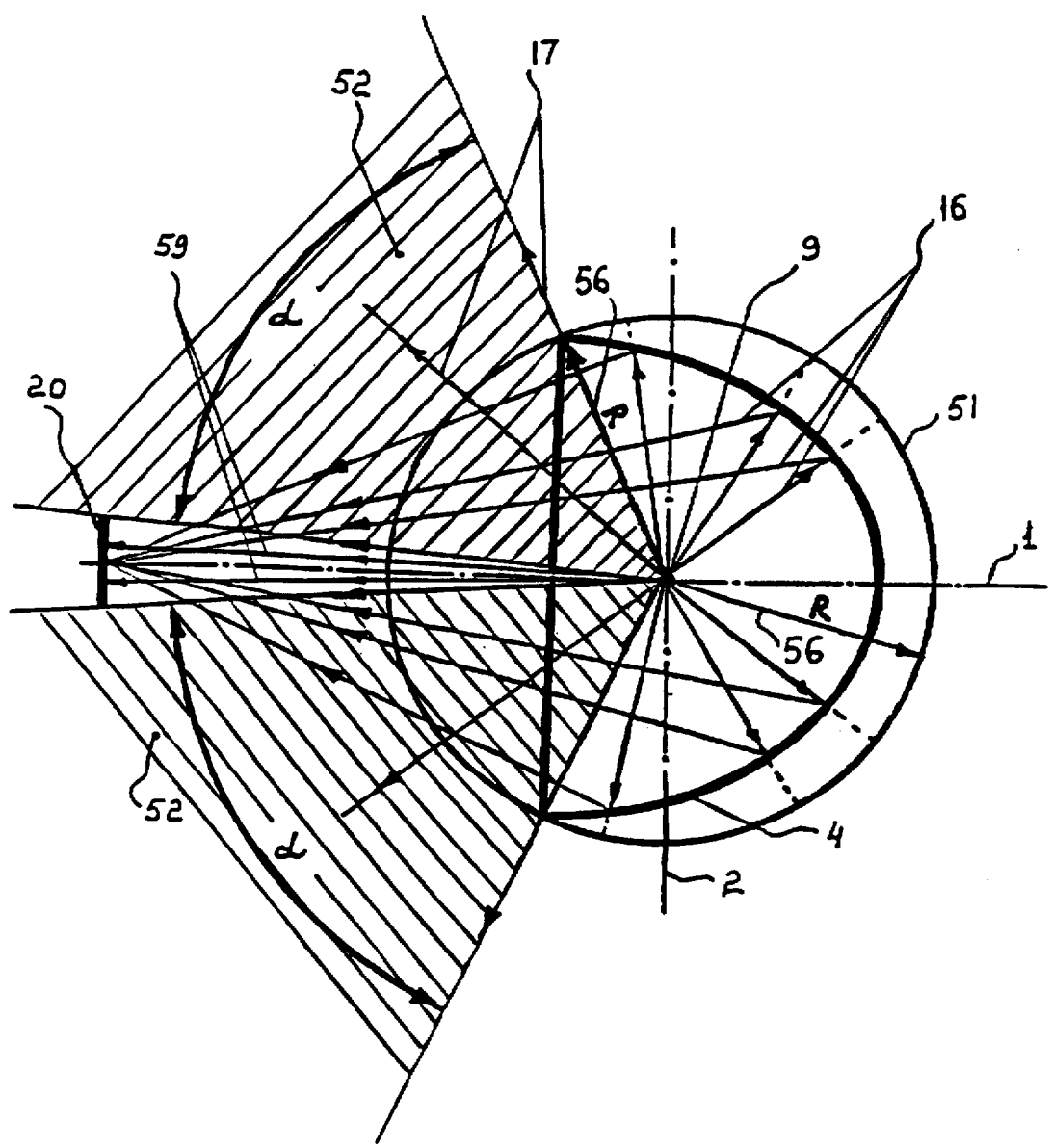
FIG. 11 illustrates a non-spatial zones of the scattered light.

On FIG. 11 are shown: 1.—a device axis; 2.—a light beam axis; 4.—a first ellipsoidal mirror; 9.—a first focus ($F_{11}$) of the first ellipsoidal mirror 4 and a second focus ($F_{22}$) of the second ellipsoidal mirror 5; 16.—a scattered light reflected from the first ellipsoidal mirror 4; 17.—a scattered light is reflected from the second ellipsoidal mirror 5; 20.—a light detector; 51.—a plane view (circle) of the scattered light distribution; 52.—a non-spatial zones of the scattered light intended for the reflection by the second ellipsoidal mirror 5; 56.—a radius of the circle 51; 59.—an unreflected scattered light detected by the light detector 20 directly.

Figure 12:
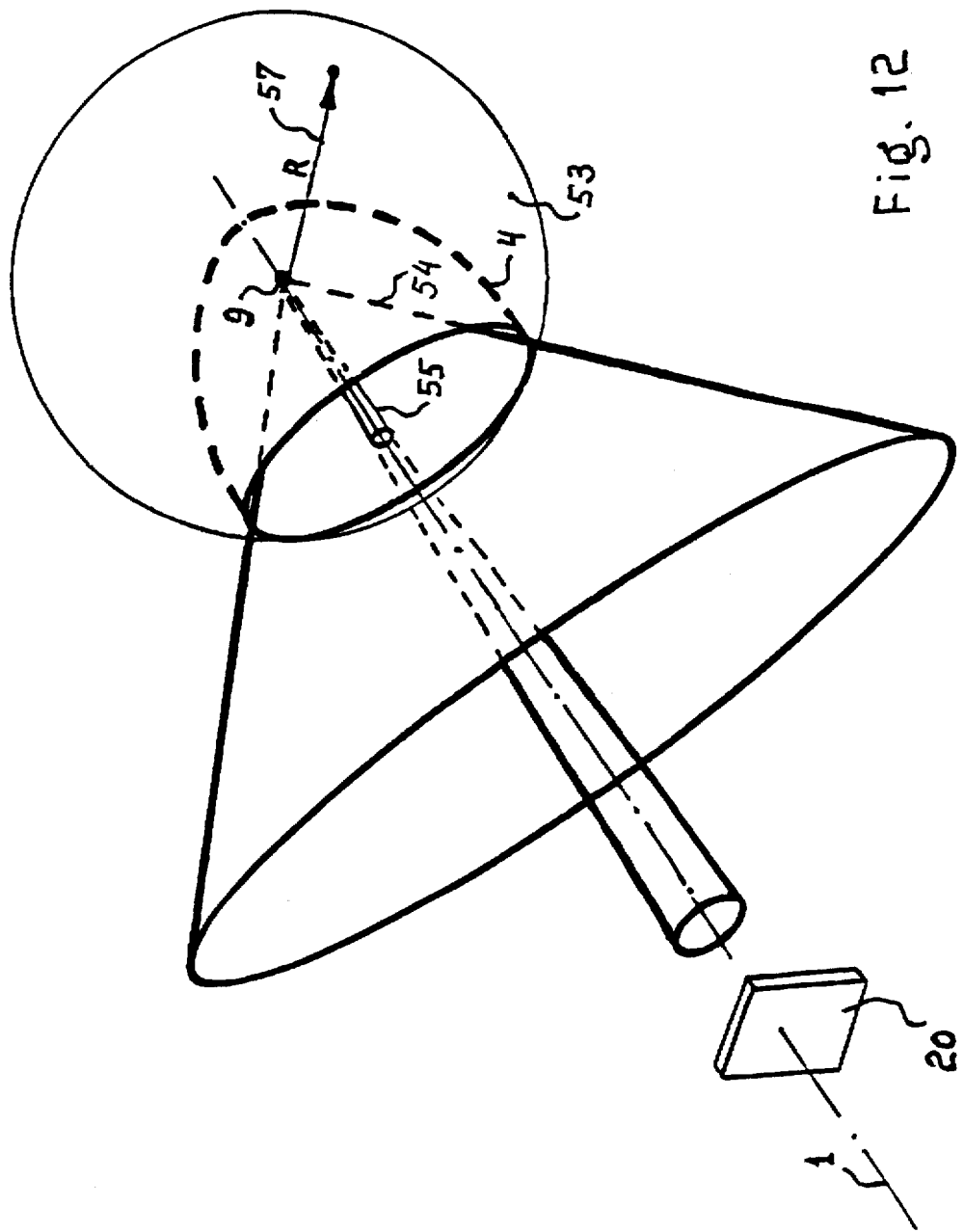
FIG. 12 is a spatial perspective view of the scattered light special conic zones.

On FIG. 12 are shown: 1.—a device axis; 4.—a first ellipsoidal mirror; 9.—a first focus ($F_{11}$) of the first ellipsoidal mirror 4 and a second focus ($F_{22}$) of the second ellipsoidal mirror 5; 20.—a light detector; 53.—a spatial view (sphere/globe) of the scattered light distribution; 54.—a cone of the scattered light intended for the reflection by the second ellipsoidal mirror 5; 55.—a cone of the unreflected scattered light 59. detected by light detector 20 directly; 57.—a radius of the sphere 53.

Figure 13:
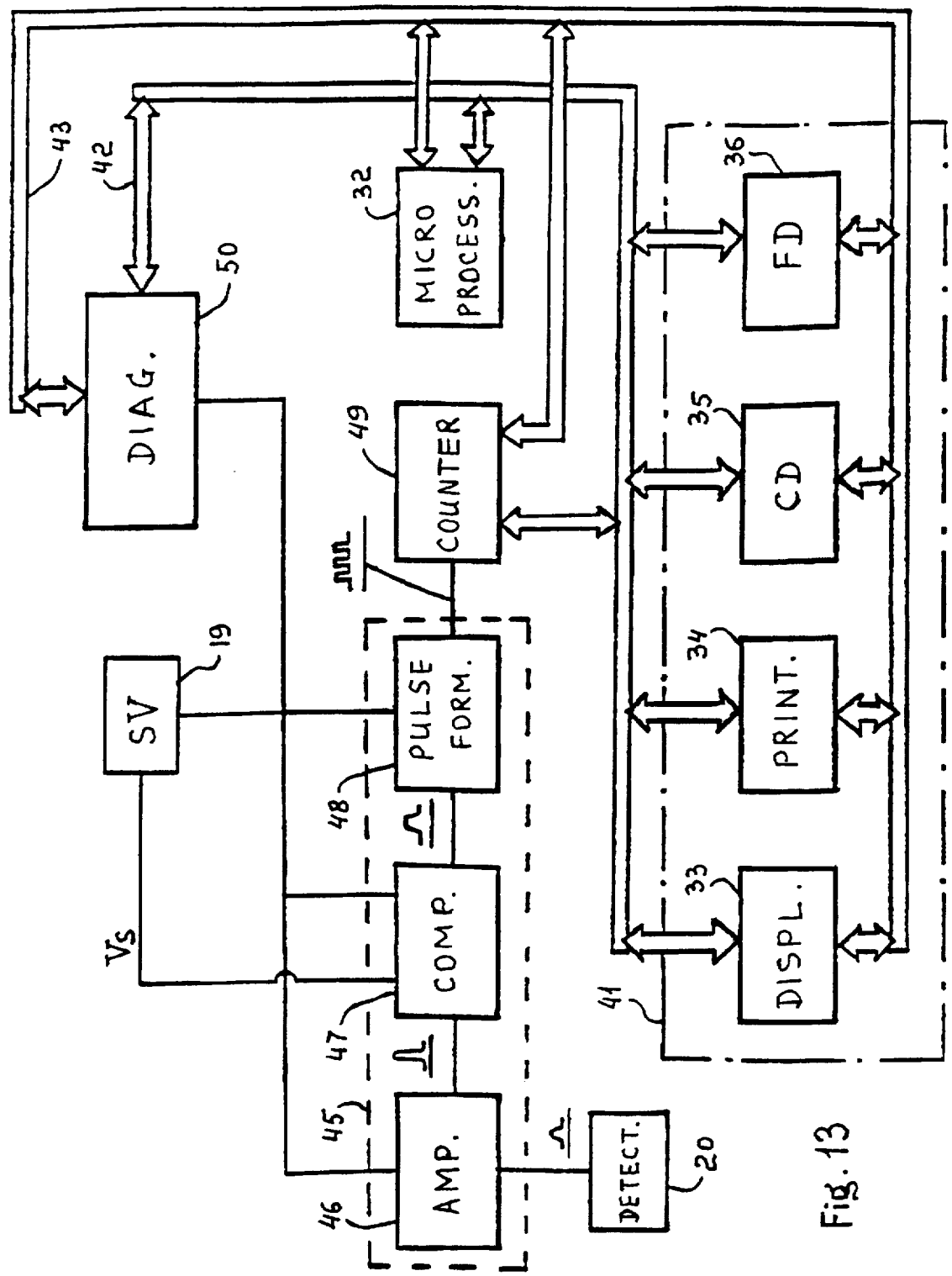
FIG. 13 is an electronic structural schematic (block-diagram) of the one channel control system.

On FIG. 13 are shown: 19.—a standard voltage means; 20.—a light detector; 32.—a microprocessor subsystem; 33.—a displaying means of the terminal means 41; 34.—a printing means of the terminal means 41; 35.—a compact disc (CD) means of the terminal means 41; 36.—a software (floppy disc) means of the terminal means 41; 41.—a terminal means; 42.—a data bus; 43.—an address bus; 45.—an analog-digital subsystem; 46.—an amplification means; 47.—a comparison means; 48.—a pulse forming means; 49.—a counting means; 50.—a diagnostic and calibration means.

Figure 14:
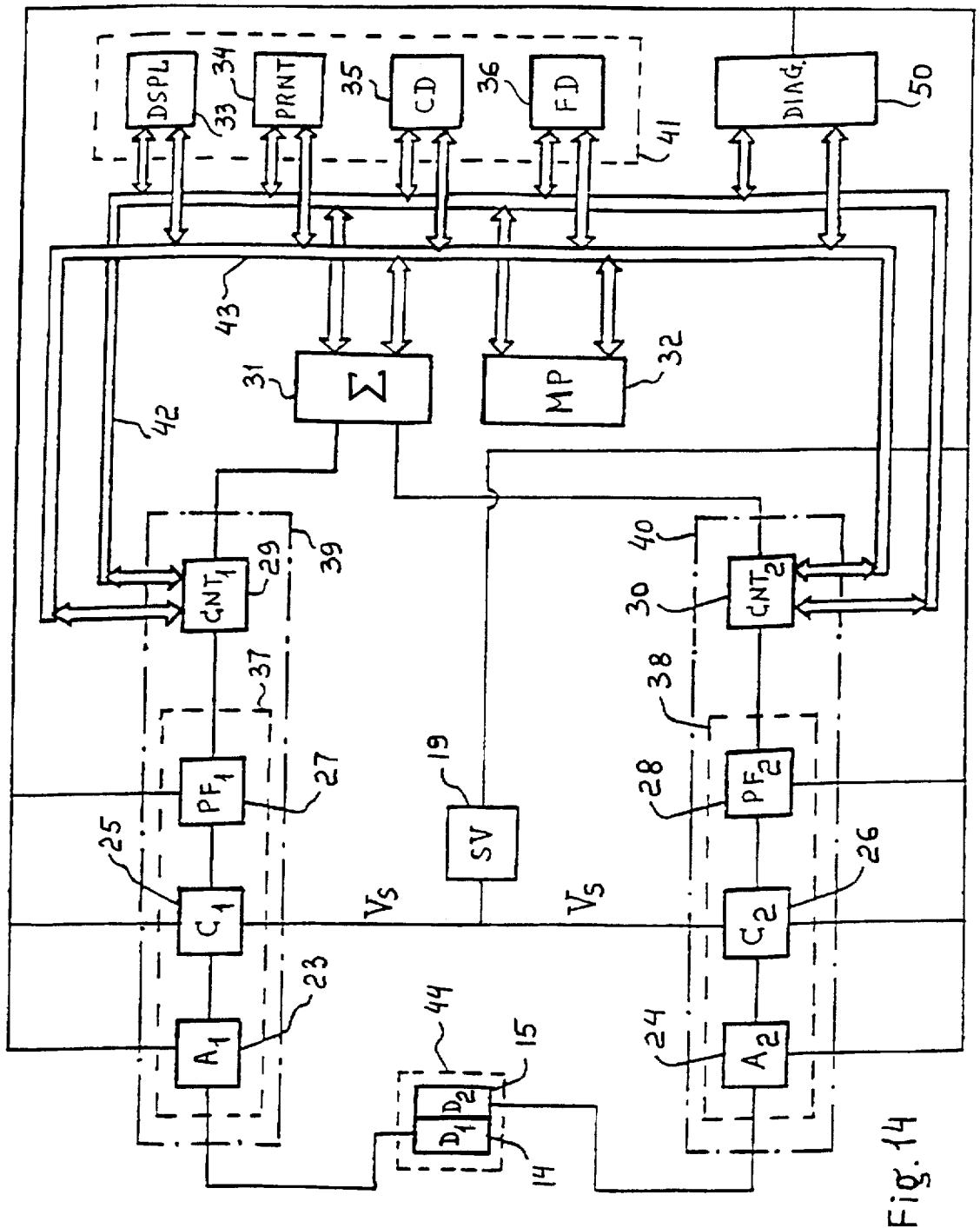
FIG. 14 is an electronic structural schematic (block-diagram) of the two channel control system.

On FIG. 14 are shown: 14.—a first light detector of the detection means 44; 15.—a second light detector of the detection means 44; 19.—a standard voltage means; 23.—an amplification means of the first channel 39; 24.—an amplification means of the second channel 40; 25.—a comparison means of the first channel 39; 26.—a comparison means of the second channel 40; 27.—a pulse forming means of the first channel 39; 28.—a pulse forming means of the second channel 40; 29.—a counting means of the first channel 39; 30.—a counting means of the second channel 40; 31.—a summarizing means; 32.—a microprocessor subsystem; 33.—a displaying means of the terminal means 41; 34.—a printing means of the terminal means 41; 35.—a compact disc (CD) means of the terminal means 41; 36.—a software (floppy disc) means of the terminal means 41; 37.—an analog-digital subsystem of the first channel 39; 38.—an analog-digital subsystem of the second channel 40; 39.—a first channel; 40.—a second channel 41.—a terminal means; 42.—a data bus; 43.—an address bus; 44.—a detection means; 50.—a diagnostic and calibration means.

SUMMARY OF THE INVENTION

This invention provides a method and device having a high sensitivity and a precision of counting and measuring particles, wherein a particle size sensitivity achieves of at least as small as 0.1 Micron. An improved method of precise counting and measuring the particulates and small bodies forms an ellipsoidal mirror system for the consideration of all scattered light plurality, comprising two different sizes ellipsoidal concentric (the same focuses of the focal points-focuses) mirrors connected towards to each other by their cross-section lateral areas. A first ellipsoidal mirror is smaller than a second ellipsoidal mirror. A light (laser) beam and a particulates and small bodies flow intersect each other inside the first ellipsoidal mirror on the device axis at the point, which belongs also to the first focus of the first ellipsoidal mirror and the second focus of the second ellipsoidal mirror. A light (photo) detector or a detection means is placed inside the second ellipsoidal mirror on the device axis at the point, which belongs to the second focus of the first ellipsoidal mirror and the first focus of the second ellipsoidal mirror, providing a detection of all scattered light plurality thereby eliminating the light noises (light background) and increasing a precision and a sensitivity of the particles counting and measuring. The light detector has an entire active photo element on both side of its body for detection of the scattered light from both sides along the device axis or can be combined of two light detectors with one active side each and connected each other by their inactive sides, forming a detection means.

By an improved method, an improved device having an ellipsoidal mirror system, a light detector or a detection means, a detector affixture and adjustment means, an electronic control system, a device axis, a particulates and small bodies flow, a light beam. The detector affixture and adjustment means, which is placed along the device axis in a peak area of the second ellipsoidal mirror, wherein is an ineffective zone of the ellipsoidal mirror system, provides an optimal position of the light detector or the detection means on the device axis for obtaining of the maximal efficiency of the scattered light detection. The electronic control system of an improved device, comprising an analog-digital subsystem, a counting means, a summarizing means for the use of the detection means, a microprocessor subsystem, a standard voltage means, a diagnostic and calibration means and a terminal means, which includes a displaying means, a printing means, a compact disc means, a software means.

DESCRIPTION OF THE PREFERRED EMBODIMENTS

Here the description of an improved method and device will be done in statics (as if the components of the improved device are suspended in the space) with description of their relative locations and connections each other. The description of the improved processes and functional operations of an improved device will be done hereafter.

An improved device, referring to FIG. 1. includes a device axis 1. a light beam (e.g., a powerful light beam or can be used a laser beam) along axis 2, a particles and small bodies flow along axis 3, a first ellipsoidal mirror 4 and a second ellipsoidal mirror 5. The axes 2 and 3 intersect each other on the device axis 1. This intersection is occurred at the point 9, which belongs to the first focus ($F_{11}$) of the first ellipsoidal mirror 4 and to the second focus ($F_{22}$) of the second ellipsoidal mirror 5, as shown on FIG. 2. The point 9 also is a point of the scattering light issue. Referring to FIG. 5, an improved device also includes a body 12 of the first ellipsoidal mirror 4 and a body 13 of the second ellipsoidal mirror 5. The light detector has an entire active element (photo element) on "m" sides of its body (where m=1, 2, 3, ....i,....) or an entire round geometric form active element, for example, a sphere, a cone (with a circular base, as a solid figure), a cylinder (with the circular base and top, as a solid figure), an ellipsoidal configuration and the others. On FIGS. 5–8 and FIGS. 10–12 is presented a light detector 20 with an entire active element on two opposite sides of its body. It means that light detector 20 detects the reflected scattered light from both sides along device axis 1 (see, for example, FIG. 6). Also the detection of the scattered light can be provided by combination of "n" light detectors with one active side each (where n=1, 2, 3, ....,j,....), forming the detection means. On FIG. 9 is presented a detection means 44, formed by combination of two light detectors 14 and 15 with one active side each. The first light detector 14 and the second light detector 15 are connected each other by their inactive sides (by the sides which are opposite to active sides). As shown on FIG. 6, the light detector 20 or the detection means 44 is placed on the device axis 1 at the point 10 which belongs to the second focus ($F_{12}$) of the first ellipsoidal mirror 4 and to the first focus ($F_{21}$) of the second ellipsoidal mirror 5. The detector affixture and adjustment means 6 is intended for affixing the light detector 20 or the detection means 44 to the ellipsoidal mirror system and for adjusting the optimal position of the light detector 20 or the detection means 44 on the device axis 1. As shown on FIGS. 5, 8, the detector affixture and adjustment means 6 is placed along an axis I and affixed to the body 13. The detector affixture and adjustment means 6 through the peak (a point "N" on an axis 1, as shown on FIG. 6) of the second ellipsoidal mirror 5 is also affixed to the light detector 20 or to the detection means 44. Considering FIG. 7, the detector affixture and adjustment means 6 is not the obstruction for detection of the scattered light by the light detector 20 or by the detector 15 of the detection means 44. Because, the detector affixture and adjustment means 6 (inside second ellipsoidal mirror 5) is placed in the ineffective (dark) zone 18, which is not involved in the effective operation of an improved device. On FIG. 7 is shown, that a zone 18 is not an active zone for any reflection processes. The detector affixture and adjustment means 6 includes an organ of the adjustment 21 and a transmission means 22, as shown on FIG. 8.

By an improved method in an improved device is formed an ellipsoidal mirror system, wherein the first (smaller) ellipsoidal mirror 4 and the second (bigger) ellipsoidal mirror 5 are connected towards to each other by their cross-section lateral sides, as if forming two different sizes of the concentric ellipsoids 7 and 8, as shown on FIG. 2. The left half of the first ellipsoid 7 belongs to the first ellipsoidal mirror 4 and the right half of the second ellipsoid 8 belongs to the second ellipsoidal mirror 5. The first focus ($F_{11}$) of the first ellipsoid 7 concurs on device axis 1 with the second focus ($F_{22}$) of the second ellipsoid 8, and the first focus ($F_{21}$) of the second ellipsoid 8 concurs on a device axis 1 with the second focus ($F_{12}$) of the first ellipsoid 7. The longitudinal axis "$2a_1$," of the first ellipsoid 7 concurs with the longitudinal axis "$2a_2$" of the second ellipsoid 8 and the lateral axis "$2b_1$," of the first ellipsoid 7 concurs with the lateral axis "$2b_2$," of the second ellipsoid 8. The focal distance "$2c$" between focus 9 and focus 10 is the same value for both ellipsoids 7 and 8.

The geometric parameters of the ellipsoids 7, 8 and the relative ellipsoidal mirrors 4, 5 can be presented by following equations:

$$\left. \begin{array}{rcl} 2a_1 & < & 2a_2 \\ 2b_1 & < & 2b_2 \\ 2c_1 & = & 2c_2 = 2c \end{array} \right\}, \quad [2]$$

where $2a_1$—a longitudinal size (length) of the first ellipsoid 7;

$2a_2$—a longitudinal size (length) of the second ellipsoid 8;

$2b_1$—a lateral size (diameter) of the first ellipsoid 7;

$2b_2$—a lateral size (diameter) of the second ellipsoid 8;

$2c_1$—a focal distance of the first ellipsoid 7;

$2c_2$—a focal distance of the second ellipsoid 8;

$2c$—a focal distance of the concentric ellipsoids 7 and 8.

The following equations can be used for calculation of the ellipsoidal mirror 5 sizes:

$$a_2 = \sqrt{a_1^2 - (b_1^2 - b_2^2)}, \quad [3]$$

where $b_2$—a priori determined value or $$b_2 = \sqrt{b_1^2 + (a_2^2 - a_1^2)}, \quad [4]$$

where $a_2$—a priori determined value.

FIG. 3 illustrates an improved method and device, in which both ellipsoidal mirrors 4 and 5 are presented as the halves of the relative ellipsoids 7 and 8, mentioned above in the description of FIG. 2, but the longitudinal size "d" of the first ellipsoidal mirror 4 is variable and can be decreased. On FIG. 4 is shown an improved device with the short first ellipsoidal mirror 4. In such device, for keeping the focal distance "2c" at same value, as mentioned of the above in equation [2], is used additional ring 11. This additional ring 11, as shown on FIG. 4, has a special inside form, for providing of the unobstructed passing of the scattered light to the second ellipsoidal mirror 5. The longitudinal size (length) "d" of the first ellipsoidal mirror 4 has limitation determined by following equation:

$$(a_1-c) < d \leq a_1, \quad [5]$$

where d—a longitudinal size of the first ellipsoidal mirror 4 (see also FIG. 2).

The width "e" of the ring 11 (see FIG. 4) depends on the longitudinal size of the first ellipsoidal mirror 4. The ellipsoidal mirror 4 can have the longitudinal size less than "$a_1$," (less than a half of ellipsoid 7 ). In this case, an angle "f" can be in the scale (0°<f<90°) and the width "e" of the ring 11 can be in the scale (e<c). Also the scale for the lateral cross-section diameter "$b_2$" of the second ellipsoidal mirror 5, considering of the above, can be (0<$b_2$<∞). But, the shorter ellipsoidal mirror 4, the wider ring 11 and the bigger angle "f". The bigger angle "f", the bigger lateral size "$b_2$" of the second ellipsoidal mirror 5. The regular utilization is:

$$b_2 - b_1 = \zeta, \quad [6]$$

where $\zeta$—a small value.

The longitudinal size of the second mirror 5 can be variable too, according mentioned of the above processes.

An improved method and device are intended to provide precise counting and measuring of the particulates (particles) and small bodies. On FIGS. 10, 11, 12 are shown that the use of an improved method and device provide counting and measuring all particles of the assaying air. FIGS. 10, 11 and 12 illustrate the directions and zones of the scattered light which are involved in the assaying of the air by an improved method and device. On FIG. 10 are shown the non-spatial directions of the scattered light distribution. FIG. 11 presents the non-spatial zones of the scattered light which are used by the second ellipsoidal mirror 5. On FIG. 12 is a spatial perspective view of scattered light and conic zones which are considered by the second ellipsoidal mirror 5. From FIG. 10 follows that the scattered light 17 (see also FIG. 6) are utilized by the second ellipsoidal mirror 5. From the plane view (circle) of the scattered light distribution 51, shown on FIG. 11, we see the areas 52 of the scattered light 17, which is reflected by the second ellipsoidal mirror 5 (see also FIG. 6). "α" is an angle of the zones 52 (on the plane view are the sectors). The point 9 belongs to the focuses $F_{11}$, $F_{22}$ and also belongs to the center of the circle 51 with a radius, 56. In the spatial view, shown on FIG. 12, the zones 52 are a spatial space between a cone 54 and a cone 55. In the spatial view the point 9 belongs to the focuses $F_{11}$, $F_{22}$ and also belongs to the center of the sphere 53 with a radius 57 (the radius 56 from FIG. 11 and the radius 57 are the same). From FIGS. 10, 11, 12 follows that the scattered light 17 (see also FIG. 6), which is between cone 54 and cone 55, is reflected by the ellipsoidal mirror 5 to the light detector 20 or the detection means 44. Thus, all plurality of the scattered light is considered.

The electronics of an improved method and device is presented by FIG. 13 and FIG. 14. Referring to the structure of electronic control system of an improved device, which is presented on FIG. 13, the improved device includes the light detector 20 connected to analog-digital subsystem 45, which comprises the consecutive connection of the amplification means 46, the comparison means 47 and the pulse forming means 48. The pulse forming means 48 is connected to the counting means 49, which by a data bus 42 and by an address bus 43 is connected to the microprocessor subsystem 32. The microprocessor subsystem 32 also by the data bus 42 and the address bus 43 or by the multiple bus (is not shown and comprising the data bus and the address bus together) is connected also to the terminal means 41 which includes the displaying means 33, the printing means 34, the compact disc (CD) means 35 and the software (floppy disc) means 36. A diagnostic and calibration means 50 by the data bus 42 and the address bus 43 is connected to the microprocessor subsystem 32. Also the diagnostic and calibration means 50 is connected to a standard voltage means 19, to the amplification means 46, to the pulse forming means 48 and to the comparison means 47, which is connected to the standard voltage means 19.

In the case of the use of the detection means 44, an improved electronic control system (see FIG. 14), as the part of an improved device, has two channels 39 and 40, which are connected through the summarizing means 31 to the microprocessor subsystem 32, as shown on FIG. 14. The first channel 39 detects the unreflected scattered light 59 directed straight to the detector 14 of the detection means 44 and also detects the scattered light reflected from both ellipsoidal mirrors 4, 5 in the ellipsoidal space between the point "M" (see FIGS. 4, 6) of the ellipsoidal mirror 4 peak on the device axis 1 and a point 10 (focuses $F_{12}$, $F_{21}$):

$$h = a_1 + c,$$ [7]

where h—a longitudinal length of the ellipsoidal space mentioned of the above and shown on FIG. 6.

The second channel 40 is intended for the detection of the scattered light reflected from the ellipsoidal mirror 5 in the ellipsoidal space between a point 10 (focuses $F_{12}$, $F_{21}$) and the point "N" of the ellipsoidal mirror 5 peak on a device axis 1:

$$g = a_2 - c,$$ [8]

where g—a longitudinal length of the ellipsoidal space mentioned of the above and shown on FIG. 6.

Referring to FIG. 14, the electronic control system of an improved device comprises a first channel 39 and a second channel 40, as was mentioned above. The first light detector 14 of the detection means 44 is connected to the amplification means 23 of the analog-digital subsystem 37 of the first channel 39. The analog-digital subsystem 37 contains also the comparison means 25 and the pulse forming means 27, which are connected in the sequence. The pulse forming means 27 is connected to the counting means 29. For the second channel 40, the second light detector 15 of the detection means 44 through the analog-digital subsystem 38, which comprises connected in the sequence the amplification means 24, the comparison means 26 and the pulse forming means 28, is connected to the counting means 30. Both counting means 29 and 30 of both channels 39, 40 are connected to the summarizing means 31. The summarizing means 31 by a data bus 42 and by an address bus 43 is connected to the microprocessor subsystem 32. The microprocessor subsystem 32 also by the data bus 42 and by the address bus 43 is connected to the counting means 29 and 30, to the displaying means 33 and to the printing means 34, to the compact disc (CD) means 35, to the software (floppy disc) means 36 and to a diagnostic and calibration means 50. Also a diagnostic and calibration means 50 is connected to the amplification means 23 of the first channel 39, to the amplification means 24 of the second channel 40, to the comparison means 25 of the first channel 39, to the comparison means 26 of the second channel 40, to the pulse forming means 27 of the first channel 39, to the pulse forming means 28 of the second channel 40. The comparison means 25 and 26 also are connected to a standard voltage means 19, which is connected to the diagnostic and calibration means 50.

An improved method and device operate as follows. The distribution of scattered light is shown on FIG. 6. The scattered light 16 reflected from the first ellipsoidal mirror 4, the unreflected scattered light 59 and the scattered light 17 reflected from the second ellipsoidal mirror 5 are then fed into the light detector 20 or into the detection means 44. As have been described above, in the area between the light detector 20 (or detection means 44) and the point "N" on device axis 1 is created a zone 18, which is inactive. Therefore, a zone 18 is used for the detector affixture and adjustment means 6, which is intended for the affixture and adjustment of light detector 20 or detection means 44 position on the device axis 1. This position is very important for detection of the maximum scattered light by light detector 20 or detection means 44. The maximal value of the detected (by light detector 20 or detection means 44) scattered light will be obtained in the case, when the mentioned above light detector 20 or detection means 44 is placed exactly at the point 10 of a focus ($F_{12}$, $F_{21}$). For such purpose is used the detector affixture and adjustment means 6. By the organ of adjustment 21 (for example, rotation clockwise or counterclockwise) through a transmission means 22 (for example, a gear) the light detector 20 or the detection means 44 moves along a device axis 1 until the maximum of the detected signals amplitude or the maximum of the counted particles will be achieved. This is in accordance with the minimum of the light noises too.

Further, the analog signals from the light detector 20 or the detection means 44 are then fed into the relative amplification means 46 or the amplification means 23 and 24, depending on the used detecting instrument (light detector 20 on FIG. 13 or detection means 44 on FIG. 14). Using the detector 20, referring to FIG. 13, the signals from light detector 20 are then fed into amplification means 46, which is intended for the increasing of the light detector 20 signals amplitudes. The increased signals from the amplification means 46 follow to the comparison means 47, which forms the analog signals accordingly to the particle sizes. The comparison means 47 forms output signals on the base of the standard voltages $V_s$ from the standard voltage means 19. These standard voltages are characterized by each particle size. These signals from the comparison means 47 follow to the pulse forming means 48. The pulse forming means 48 creates the digital (square) form of the pulses and the appropriate amplitudes of the signals for the further digital processing. It means that the pulse forming means 48 transforms the amplitudes and the form of the analog signals to the acceptable amplitudes and form of the digital signals, accordingly the relative parameters of the analog signals. This provides the correctness and authenticity of the digital data. The counting means 49 counts the pulses from the pulse forming means 48 and transfers the digital data to the microprocessor subsystem 32, which processes the digital data correspondingly to the programmed control commands by the compact disc means 35, or the software means 36 or EPROM chip (housed inside microprocessor subsystem 32 and not shown). The digital control data exchange between electronic means, such as the microprocessor subsystem 32, the counting means 49, a diagnostic and calibration means 50, the terminal means 41, is realized by the data bus 42 and the address bus 43. Also the processed digital data is then fed into displaying means 33 and printing means 34 of the terminal means 41. The diagnostic and calibration means 50 is intended for operative periodical self testing of the electronic control system components (means) and a self calibration. All information for diagnostics (testing, calibration) is processed by microprocessor subsystem 32 and diagnostic and calibration means 50 and is distributed correspondently to the relative electronic means of this electronic control system, as shown on FIG. 13 and as have been mentioned of the above.

With the use of the detection means 44, referring to FIG. 14, the processing of the information follows in the sequence as have been described of the above (referring to FIG. 13), but the scattered light is detected by two detectors 14 and 15 of the detection means 44, and the signals from the detectors 14 and 15 follow to the two relative identical channels 39 and 40, which are adequate with the described of the above (referring to FIG. 13), but for receiving of the full information about the characteristics of the particles and small bodies, the signals from counting means 29 and 30 follow to the summarizing means 31, which after summarizing of the pulses from both counting means 29 and 30 of both channels 39 and 40, transfers this data to the microprocessor subsystem 32 for processing it. The diagnostic and calibration means 50 performs the same functions, as have been mentioned above in the description of the electronic control system presented on FIG. 13, but for two identical channels 39 and 40.

CONCLUSION, RAMIFICATIONS AND SCOPE

Accordingly the reader will see that, according to the invention, I have provided a precise and effective method and device, which provide counting and measuring of the all particulates and small bodies of the assayed air. An improved method and device provide authenticity of the real quantity and sizes of the particulates and small bodies in the assayed mixture of air or, for example, gas, because all plurality of the scattered from particulates and small bodies light is considered. Also the improved method and device provide authenticity, because eliminate light noises (light background) inside an improved device. The improved device is simple to produce and easer to use considering the presence of the self diagnostic and calibration means.

While the above description contains many specificities, these should not be construed as limitations on the scope of the invention, but as exemplifications of the presently-preferred embodiments thereof. Many other ramifications are possible within the teachings to the invention. For example, an improved method and device provide the revelation of the defects (out of order) any parts (components) of the means and subsystems in the improved device by periodical self testing, using the diagnostic and calibration means. It provides eradication of the defects on the earliest stage, because, for example, if one amplifier of the amplification means will be out of order (the previous devices, mentioned in the description of the prior art, will continue to operate and still indicate information about particles quantity and sizes, but it will be incorrect information), an improved device will reveal this defect by diagnostics. Another ramification can be presented by calibration field. It is known, that the particle counting and measuring devices are the subjects for a calibration by manufacturer, for example, once a six-eight months, but by the improved method and device the calibration can be provided by user any time, using the built-in diagnostic and calibration means, and not often than once in eighteen-twenty four months the device can be sent to the manufacturer just for inspection of the ellipsoidal mirror surface and laser means conditions.

Thus the scope of the invention should be determined by the appended claims and their legal equivalents, and not by examples given.

What is claimed is:

1. A method for precise counting and measuring a particulates and small bodies illuminated by a light beam and including the steps, wherein:

detecting a scattered light by an ellipsoidal mirror system, comprising a first ellipsoidal mirror and a second ellipsoidal mirror, which is bigger than said first ellipsoidal mirror, wherein said first ellipsoidal mirror and said second ellipsoidal mirror are connected towards to each other by cross-section lateral areas of said first ellipsoidal mirror and said second ellipsoidal mirror, wherein said ellipsoidal mirror system is placed along a device axis, which concurs with the major axes of said first ellipsoidal mirror and said second ellipsoidal mirror, wherein a first focus of said first ellipsoidal mirror concurs on said device axis with a second focus of said second ellipsoidal mirror and a second focus of said first ellipsoidal mirror concurs on said device axis with a first focus of said second ellipsoidal mirror;

detecting said scattered light which is occurred inside said first ellipsoidal mirror on said device axis by intersection of said light beam with a particulates and small bodies flow at a point of said second focus of said second ellipsoidal mirror, which belongs also to said first focus of said first ellipsoidal mirror;

detecting said scattered light by a light detector or by a detection means, which is placed inside said second ellipsoidal mirror on said device axis at a point of said first focus of said second ellipsoidal mirror, which belongs also to said second focus of said first ellipsoidal mirror.

2. The method of claim 1, wherein detecting said scattered light by said light detector or by said detection means, which is affixed to said ellipsoidal mirror system and a position of said light detector or said detection means on said device axis is adjusted by a detector affixture and adjustment means, which is placed in a peak area of said second ellipsoidal mirror.

3. The method of claim 1, wherein detecting said scattered light by said light detector, having an entire photo element on m=1, 2, 3, . . . . i, . . . sides of a body of said light detector.

4. The method of claim 1, wherein detecting said scattered light by said light detector, having an entire round geometric form photo element.

5. The method of claim 1, wherein detecting said scattered light by said detection means, comprising n=1, 2, 3, . . . . , j, . . . light detectors, having a photo elements placed on one side of their bodies, and wherein these light detectors are connected each other by an inactive sides of their bodies.

6. The method of claim 5, wherein detecting said scattered light by said detection means, wherein a processed signals from said n=1, 2, 3, . . . j, . . . light detectors are summarized.

7. A device for precise counting and measuring a particulates and small bodies, comprising an ellipsoidal mirror system including a first ellipsoidal mirror and a second ellipsoidal mirror connected towards to each other by cross-sectional lateral areas, a light detector, a detector affixture and adjustment means, an one channel electronic control system, a device axis, a particulates and small bodies flow, a light beam, wherein said light beam intersects said particulates and small bodies flow on said device axis inside said first ellipsoidal mirror at a point, which belongs to a second focus of said second ellipsoidal mirror and to a first focus of said first ellipsoidal mirror, wherein said first ellipsoidal mirror is smaller than said second ellipsoidal mirror, in which on said device axis at a point, which belongs to a first focus of said second ellipsoidal mirror and to a second focus of said first ellipsoidal mirror, is placed said light detector, and wherein said detector affixture and adjustment means, having an organ of adjustment and a transmission means, is placed along said device axis in a peak area of said second ellipsoidal mirror.

8. The device of claim 7, wherein said light detector, comprising an entire photo element on two opposite sides of its body.

9. The device of claim 8, wherein said light detector is connected to an amplification means of said analog-digital subsystem of an one channel electronic control system.

10. The device of claim 7, wherein said one channel electronic control system, comprising an amplification means, which is connected to a diagnostic and calibration means and to a comparison means, which is connected to said diagnostic and calibration means, to a standard voltage means, which is connected to said diagnostic and calibration means, and to a pulse forming means, which is connected to said diagnostic and calibration means and to a counting means, which by a data bus and by an address bus is connected to a microprocessor subsystem, which by said data bus and by said address bus also is connected to a display means, to a printing means, to a compact disc means, to a software means, which belong to a terminal means, and to said diagnostic and calibration means, wherein said amplification means, said comparison means and said pulse forming means belong to an analog-digital subsystem.

11. The device of claim 9, wherein said data bus and said address bus are united in a multiple bus and a digital data exchange in said one channel electronic control system is provided by said multiple bus.

12. A device for precise counting and measuring a particulates and small bodies, comprising an ellipsoidal mirror system including a first ellipsoidal mirror and a second ellipsoidal mirror connected towards to each other by cross-sectional lateral areas, a detection means, a detector affixture and adjustment means, a two channel electronic control system, a device axis, a particulates and small bodies flow, a light beam, wherein said light beam intersects said particulates and small bodies flow on said device axis inside said first ellipsoidal mirror at a point, which belongs to a second focus of said second ellipsoidal mirror and to a first focus of said first ellipsoidal mirror, wherein said first ellipsoidal mirror is smaller than said second ellipsoidal mirror, in which on said device axis at a point, which belongs to a first focus of said second ellipsoidal mirror and to a second focus of said first ellipsoidal mirror, is placed said detection means, and wherein said detector affixture and adjustment means, having an organ of adjustment and a transmission means, is placed along said device axis in a peak area of said second ellipsoids mirror.

13. The device of claim 12, wherein said detection means, comprising a first light detector and a second light detector, wherein said first light detector of said detection means and said second light detector of said detection means are connected each other by an inactive sides of their bodies, wherein said inactive sides are opposite to an active sides of said first light detector and said second light detector.

14. The device of claim 13, wherein said first light detector of said detection means is connected to an amplification means of a first channel of said two channel electronic control system and a second light detector of said detection means is connected to said amplification means of a second channel of said two channel electronic control system.

15. The device of claim 12, wherein said two channel electronic control system, comprising a diagnostic and calibration means, a summarizing means, a terminal means, a first channel, a second channel, a microprocessor means, a standard voltage means, an analog-digital subsystem of said first channel, having connected in sequence an amplification means of said first channel, a comparison means of said first channel and a pulse forming means of said first channel, an analog-digital subsystem of said second channel, having connected in sequence an amplification means of said second channel, a comparison means of said second channel, and a pulse forming means of said second channel, wherein a counting means of said first channel is connected to said pulse forming means of said first channel and to said summarizing means, wherein a counting means of said second channel is connected to said pulse forming means of said second channel and to said summarizing means, which by a data bus and by an address bus is connected to said microprocessor means, which also by said data bus and by said address bus is connected to a displaying means of said terminal means, to a printing means of said terminal means, to a compact disc means of said terminal means, to a software means of said terminal means, to said counting means of said first channel, to said counting means of said second channel and to said diagnostic and calibration means, which is connected to said amplification means of said first channel, to said amplification means of said second channel, to said pulse forming means of said first channel, to said pulse forming means of said second channel, to said comparison means of said first channel and to said comparison means of said second channel, which is connected to said comparison means of said first channel and to said standard voltage means, which is connected to said diagnostic and calibration means.

16. The device of claim 14, wherein said data bus and said address bus are united in a multiplexed bus and a digital data exchange in said two channel electronic control system is provided by said multiple bus.

* * * * *

UNITED STATES PATENT AND TRADEMARK OFFICE
CERTIFICATE OF CORRECTION

PATENT NO. : 5,767,967
DATED : June 16, 1998
INVENTOR(S) : Aleksandr L. Yufa

It is certified that error appears in the above-indentified patent and that said Letters Patent is hereby corrected as shown below:

Column 6, line 18 of the top, change '(the same focuses' to -(the same locuses-

Column 13, line 8 of the bottom, change 'of claim 9' to -of claim 10-

Column 13, line 26 of the bottom, change 'of said analog-digital' to -of an analog-digital- Column 14, line 4 of the bottom, change 'of claim 14' to -of claim 15-

Column 14, line 27 of the top, change 'a second light detector' to -said second light detector- Column 14, line 28 of the top, change 'said amplification means' to -an amplification means- Column 14, line 36 of the top, change 'having connected' to -including connected- Column 14, line 26 of the top, change 'of said two channel' to -of a two channel-

UNITED STATES PATENT AND TRADEMARK OFFICE
CERTIFICATE OF CORRECTION

PATENT NO. : 5,767,967
DATED : June 16, 1998
INVENTOR(S) : Aleksandr L. Yufa

It is certified that error appears in the above-indentified patent and that said Letters Patent is hereby corrected as shown below:

Column 4, line 8 of the bottom, change 'and a first focus ($F_{22}$)' to -and a second focus ($F_{22}$)-

Column 4, line 6 of the bottom, change 'a second focus ($F_{21}$)' to -a first focus ($F_{21}$)-

Column 9, line 26 of the bottom, change 'multiple bus' to -multiplexed bus-
Column 13, line 5 of the bottom, change 'multiple bus' to -multiplexed bus-
Column 13, line 7 of the bottom, change 'multiple bus' to -multiplexed bus-
Column 14, line 1 of the bottom, change 'multiple bus' to -multiplexed bus- Column 12, line 8 of the top, change 'and easer to' to -and easier to- Signed and Sealed this Eighth Day of September, 1998

BRUCE LEHMAN

*Attest:*

*Attesting Officer*        Commissioner of Patents and Trademarks